US00PP36132P2

(12) United States Plant Patent
Carruth

(10) Patent No.: US PP36,132 P2
(45) Date of Patent: Sep. 24, 2024

(54) GRANDIFLORA ROSE PLANT NAMED 'WEKalmylcas'

(50) Latin Name: *Rosa hybrida*
Varietal Denomination: WEKalmylcas

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 0 days.

(21) Appl. No.: 18/540,248

(22) Filed: Dec. 14, 2023

(51) Int. Cl.
*A01H 5/02* (2018.01)
*A01H 6/74* (2018.01)

(52) U.S. Cl.
USPC ..... Plt./138

(58) Field of Classification Search
USPC ..... Plt./138
See application file for complete search history.

(56) References Cited

U.S. PATENT DOCUMENTS

PP23,476 P2 3/2013 Carruth
PP29,273 P2 5/2018 Fryer

OTHER PUBLICATIONS

Bedard, C., "Grandiflora Rose Plant Named "Weksecjuc"," U.S. Appl. No. 18/390,244, filed Dec. 20, 2023, 10 pages.
Bedard, C., "Shrub Rose Plant Named "Wekblufstow"," U.S. Appl. No. 18/533,666, filed Dec. 8, 2023, 13 pages.
Carruth, T., "Hybrid Tea Rose Plant Named "Wekmotonton"," U.S. Appl. No. 18/541,817, filed Dec. 15, 2023, 11 pages.
Make Me Blush TM, "Weeks Roses," 2024 Wholesale Rose Catalog, 2024, 100 pages.

*Primary Examiner* — Susan McCormick Ewoldt
*Assistant Examiner* — Zachariah Allan Kay
(74) *Attorney, Agent, or Firm* — McKee, Voorhees & Sease, PLC

(57) ABSTRACT

A new variety of Grandiflora rose suitable for garden decoration, having flowers of medium pink coloration.

1 Drawing Sheet

Classification: The present invention relates to a new *Rosa hybrida* plant.

Variety denomination: The new plant has the varietal denomination 'WEKalmylcas'.

BACKGROUND OF THE INVENTION

This invention relates to a new and distinct variety of Grandiflora Rose. It has as its seed parent the variety known as 'FRYrapture' (U.S. Plant Pat. No. 29,273) and as its pollen parent the variety known as 'WEKcibamcala' (not patented). It was hybridized by Thomas F. Carruth.

SUMMARY OF THE INVENTION

Among the features which distinguish the new variety from other presently available and commercial rose cultivars known to the inventor are the following combinations of characteristics: its elegant flowers of medium pink coloration, its abundant blooms and its excellent color stability throughout the life of the flower. The plant has an upright bushy moderately spreading growing habit, suitable for outdoor garden decoration.

Asexual reproduction of the new variety by budding as performed in Kern County, California, shows that the foregoing and other distinguishing characteristics come true to form and are established and transmitted through succeeding asexual propagations. 'WEKalmylcas' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'FRYrapture' by the following combination of characteristics: whereas 'WEKalmylcas' bears very double flowers (about 31 to 82 petals) of medium pink coloration, 'FRYrapture' bears flowers of dark even pink coloration with lesser petalage (about 30 to 50 petals). The new variety has an upright bushy moderately spreading medium height growing habit (about 117 to about 155 cm. in height), whereas the seed parent has a bushy upright significantly taller growing habit (about 190 to about 240 cm. in height).

The new variety may be distinguished from its pollen parent, 'WEKcibamcala' by the following combination of characteristics: whereas 'WEKalmylcas' bears flowers of medium pink coloration with a moderate fruity to spicy fragrance, 'WEKcibamcala' bears flowers of orange-pink blended coloration with lighter reverse and with mild fragrance. The new variety has an upright bushy moderately spreading medium height growing habit (about 117 to about 155 cm. in height), whereas the pollen parent has a bushy rounded moderately spreading significantly shorter growing habit (about 80 to about 100 cm. in height).

COMPARISON WITH THE CLOSEST COMMERCIALLY AVAILABLE CULTIVAR

The new variety may be distinguished from its closest commercially available cultivar, 'WEKmerewby' (U.S.

Plant Pat. No. 23,476) by the following combination of characteristics: whereas 'WEKalmylcas' bears very double flowers (about 31 to 82 petals) with a moderate fruity to spicy fragrance, 'WEKmerewby' bears flowers with significantly lesser petalage (about 26 to 38 petals) with a very strong damask to somewhat fruity fragrance. The new variety has an upright bushy moderately spreading medium height growing habit (about 117 to about 155 cm. in height), whereas the closest commercially available cultivar has an upright significantly taller growing habit (about 170 to about 190 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, California in the month of November. Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Wasco, California in the month of November. Phenotypic expression may vary with environmental, cultural and climatic conditions, as well as differences in conditions of light and soil.

Flower

The new variety usually bears its flowers singly, sometimes in clusters of two to seven or more per stem. Flowers may be borne in regular rounded clusters on strong short to medium length stems (about 13 to about 58 cm.). The cluster ranges from about 12.5 to about 16.5 cm. in diameter. Outdoors, the plant blooms abundantly and nearly continuously during the growing season. The flowers have a moderate fruity to spicy fragrance.

Bud

The peduncle is about 2.3 to about 5.6 cm. in length, of slender to average caliper (about 0.2 to about 0.4 cm. in diameter), and usually erect. It is smooth with very few stipitate glands and very few hairs. Peduncle color is between 146C and 152A often moderately suffused, especially on the side exposed to the sun, with between 187B and 187A.

Before the calyx breaks, the bud is about 1.1 to about 1.6 cm. in diameter at the widest point, about 1.5 to about 2.0 cm. in length, and pointed to somewhat ovoid in shape. The surface of the bud bears between 4 to 7 foliaceous appendages with some hairs, usually with slender entire foliaceous parts extending beyond the tip of the bud about ½ or more of its length. Bud color is between 138A and 146B sometimes moderately suffused, especially on the side exposed to the sun, with between 187B and 187A.

The sepals are 5 per flower, about 1.4 to about 3.9 cm. in length and about 0.6 to about 1.0 cm. in width at the widest point. The outer surface color of the sepal is between 138A and 146B sometimes moderately suffused, especially on the side exposed to the sun, with between 187B and 187A. The outer surface of the sepal is smooth and bears between 0 to 3 foliaceous appendages with some hairs. The inner surface color of the sepal is near 146D broadly bordered by near 137B. After the sepals open, the inner surface color is often heavily suffused, especially on the area exposed to the sun, with between 187B and 187A. The inner surface of the sepal is covered with fine wooly tomentum; sepal margins are entire and lined with few stipitate glands and some hairs. The sepals are moderately permanent, and usually straight in shape with acute apices.

The receptacle of the flower is of moderately short to medium length (about 0.3 to about 0.6 cm.) and somewhat thin to average in caliper (about 0.5 to about 0.9 cm. in diameter). The receptacle is urn-shaped in form. Its surface is smooth with moderately thick fleshy walls. The receptacle color is between 146C and 146B.

As the petals open (after the calyx breaks), the bud is about 1.7 to about 2.3 cm. in diameter at the widest point, about 2.3 to about 3.0 cm. in length, and pointed to ovoid in form. The color of the under surfaces of the newly opened petals is between 53D and 54A sometimes moderately suffused with between 59C and 60B. At the point where the petal attaches, there is a somewhat large zone of between 150C and 154C. The color of the upper surfaces of the newly opened petals is between 59D and 54A. At the point where the petal attaches, there is a somewhat large zone of between 1C and 154C.

Bloom

When fully open, the bloom ranges from about 7.3 to about 12.6 cm. in diameter. Petalage is very double with about 31 to 82 petals and about 3 to 20 petaloids irregularly arranged. When partially open, the bloom form is moderately high centered to cupped, and the petals are moderately tightly spiraled to cupped with petal edges somewhat reflexed outward. When fully open, the bloom form is cupped, and the petals are loosely cupped to slightly undulated with petal edges somewhat reflexed outward. Sometimes some of the intermediate and inner petals are folded along the midrib.

Petals

The substance of the petals is moderately heavy and of medium to somewhat thick thickness, with upper surfaces moderately satiny and under surfaces moderately shiny. The petals are about 2.8 to about 5.4 cm. in length and about 2.3 to about 6.2 cm. in width at the widest point. Petal margins are entire.

The outer petals are nearly rounded to somewhat obovate in shape with rounded apices and sometimes slightly notched with one notch.

The inner petals are moderately obovate in shape with rounded apices.

Petaloids are about 0.7 to about 3.6 cm. in length and about 0.3 to about 2.7 cm. in width at the widest point. Petaloids are irregularly shaped moderately obovate to somewhat oblanceolate to subulate with rounded to sometimes lacerated apices.

Newly Opened Flower

The under-surface color of the outer petals is between 57D and 66D. At the point where the petal attaches, there is a moderately small zone of near 10D. The upper surface color of the outer petals is between 61C and 65A. At the point where the petal attaches, there is a moderately large zone of between 2C and 3D.

The under-surface color of the intermediate and inner petals is between 58B and 55A. The upper surface color of the intermediate and inner petals is between 57B and 55A.

The under and upper surface colors of the petaloids are similar in coloration to the upper and under surfaces of the intermediate and inner petals.

The general tonality of the newly opened flower is between 57B and 55A.

Three-Day-Old Flower

The under-surface color of the outer petals is between 66D and 62A. At the point where the petal attaches, there is a moderately small zone of between 154D and 1D. The upper surface color of the outer petals is between 66C and 65A. At the point where the petal attaches, there is a moderately large zone of between 1D and 154D.

The under-surface color of the intermediate and inner petals is between 63B and 62A. The upper surface color of the intermediate and inner petals is between 61C and 57D.

The under and upper surface colors of the petaloids are similar in coloration to the upper and under surfaces of the intermediate and inner petals.

The general tonality of the three-day-old flower is between 61C and 57D.

On the spent bloom, the petals usually drop off cleanly.

In November in Wasco, California, blooms on the bush growing outdoors generally last about four to five days. Cut roses from plants grown outdoors and kept at normal indoor living temperatures generally last about four to five days.

Male Reproductive Organs

Stamens are many in number (average about 175) and are arranged regularly about the pistils; a few are mixed with petaloids. The filaments are of somewhat short to medium length (about 0.3 to about 1.1 cm.) most with anthers. Filaments are between 1A and 5A in color. The anthers are somewhat small for the class and all open approximately at the same time. Anther color when immature is near 19A on the external part and near 11D on the internal part. Anther color at maturity is near 164C on the external part and near 200B on the internal part. Pollen is moderate and between 18C and 19C in color.

Female Reproductive Organs

Pistils vary in number (average about 110). The styles are moderately even, somewhat short to average in length (about 0.4 to about 1.0 cm.), moderately heavy in caliper, and loosely bunched to somewhat separated. Stigma color is between 18D and 13D. Style color is between 1C and 154C usually heavily suffused near the top with near 60A. Ovaries are usually all enclosed in the calyx. The ovaries are of small size and between 158A and 150D in color.

Hips are of somewhat short to average length (about 0.7 to about 1.4 cm.), cup-shaped to somewhat globular in form with a flat top, and between 53A and 44A in color when ripe. The hip surface is smooth with moderately thick fleshy walls.

The seeds are irregularly rounded, smooth in texture, approximately 5 to about 22 per hip, about 0.4 to about 0.6 cm. in diameter at the widest point and near 164C in color.

Foliage

The compound leaves are usually comprised of three to seven leaflets and are borne abundantly. The five-leaflet leaves are about 9.0 to about 15.5 cm. in length and about 7.2 to about 12.5 cm. in width at the widest point, moderately leathery to somewhat crisp in texture on both sides, and glossy in finish on the upper side and semi-glossy in finish on the underside. The leaves have a pinnate venation pattern. The terminal leaflets are about 4.5 to about 8.1 cm. in length and about 2.5 to about 4.4 cm. in width at the widest point, shaped oval with acute apices and rounded bases. Their margins are usually simply serrate.

The upper surface color of the mature leaf is between 137A and 147A. The under-surface color of the mature leaf is between 147B and 147C. The under and upper colors of the leaf veins on the mature leaf are similar in coloration to the upper and under surfaces colors of the mature leaf. The upper surface color of the young leaf is between 137B and 137A, often heavily suffused with between 187B and 187A. The under-surface color of the young leaf is between 146B and 147C, often moderately suffused with between 187B and 187A. The under and upper colors of the leaf veins on the young leaf are similar in coloration to the upper and under surfaces colors of the young leaf.

The rachis is about 2.5 to about 5.3 cm. in length, about 0.1 to about 0.2 cm in width at the widest point, and sometimes smooth, sometimes rough. The upper side is deeply grooved with few hairs on the edges of the grooves. The underside of the rachis is sometimes smooth, sometimes rough with few small prickles. The rachis color is near 145B on the underside and near 146D on the upper side, often heavily suffused on the young leaves with between 187B and 187A.

The stipules are about 1.4 to about 2.1 cm. in length and of somewhat narrow to medium width (about 0.4 to about 0.7 cm.) with medium length straight points that usually turn out at an angle of more than 45 degrees and sometimes recurve toward the stem. The under and upper surface color of the stipule is near 137B. The upper and under surfaces of the stipules are smooth in texture.

The petiole is somewhat light in caliper and smooth. The upper side is deeply grooved with few hairs on the edges of the grooves. The under side of the petiole is smooth. The petiole is about 0.3 to about 2.1 cm. in length and about 0.1 to about 0.2 cm in width at the widest point. The petiole color is near 145B on the underside and near 146D on the upper side, often heavily suffused on the young leaves with between 187B and 187A.

The plant displays an above average degree of resistance to powdery mildew (*Sphaerotheca pannosa*), downy mildew (*Peronospora sparsa*) and rust (*Phragmidium* sp.) as compared to other commercial varieties grown under comparable conditions in Wasco, California. The plant's winter hardiness and drought/heat tolerance are yet to be determined.

Growth

The plant has an upright bushy moderately spreading medium height growing habit (about 117 to about 155 cm. in height and about 107 to about 157 cm. spread at the widest point), with full branching. It displays moderately vigorous growth and the canes are of medium to somewhat heavy caliper for the class (about 1.3 to about 2.2 cm. in diameter at the widest point).

The color of the major stems is between 146B and 146C. The major stems are rough in texture and they bear some large prickles that are about 0.5 to about 0.9 cm. in length. The large prickles are angled slightly downward with a long somewhat broad oval base; prickle color is between 165C and 164B sometimes lightly suffused with between 201C and 201D. The major stem bears few small prickles of similar shape and coloration.

The color of the branches is between 146C and 146D. The branches are rough in texture and they bear some large prickles which are of similar size and shape to the large prickles on the major stems; prickle color is between 153A and 152D often moderately suffused with between 187C and 187D. The branches bear very few small prickles of similar shape and coloration.

The color of the new shoots is between 146C and 146D often heavily suffused with between 187B and 187A. The new shoots are rough in texture and they bear some large prickles which are of similar size and shape to the large prickles on the major stems; prickle color is between 153A and 152D often heavily suffused with between 187B and 187C to as dark as near 187A. The shoots bear very few small prickles of similar shape and coloration.

I claim:

1. A new and distinct Grandiflora rose plant of the variety designated 'WEKalmylcas' substantially as described and illustrated herein.

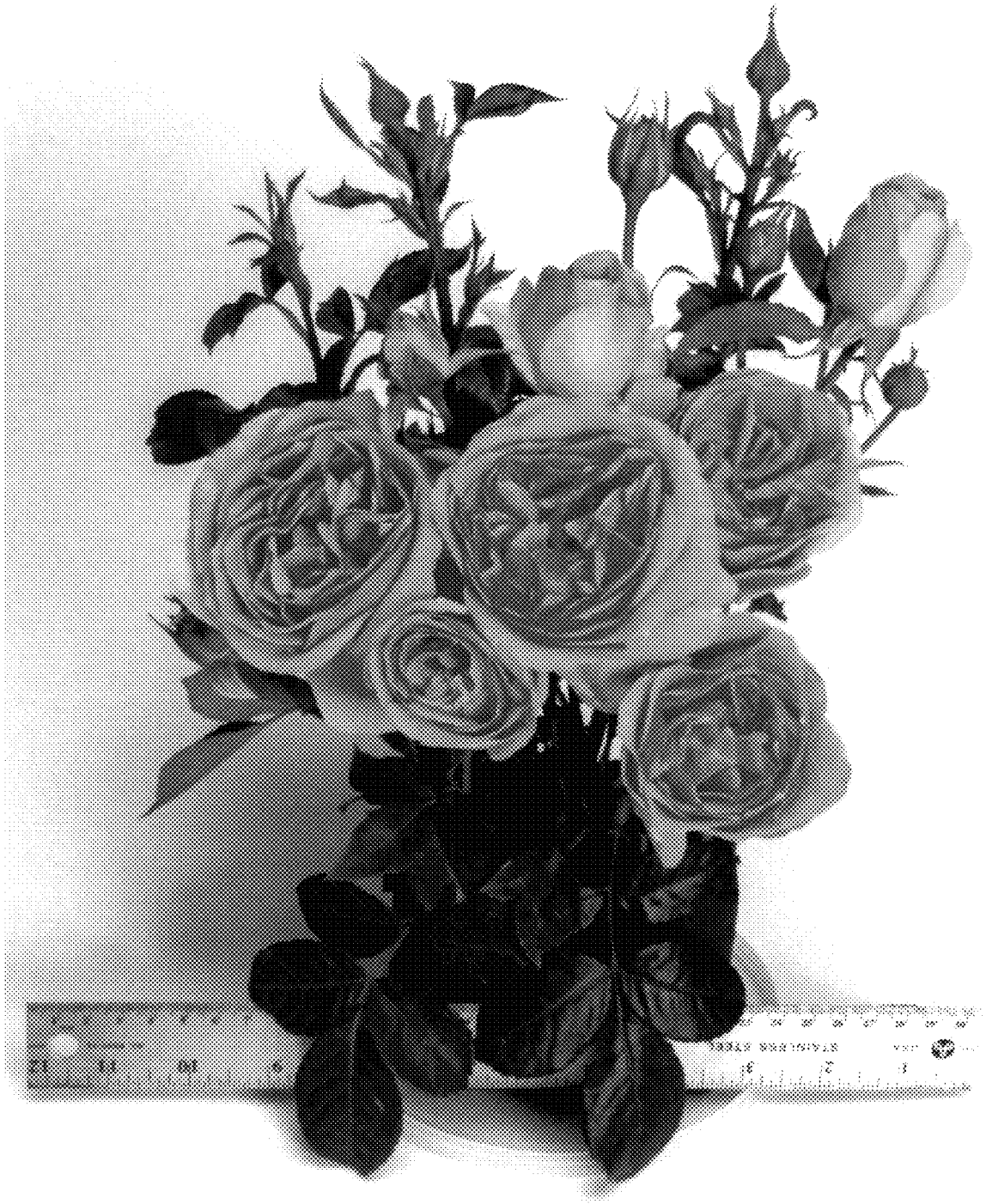

* * * * *